United States Patent [19]
Barenholz et al.

[11] Patent Number: 6,066,331
[45] Date of Patent: May 23, 2000

[54] METHOD FOR PREPARATION OF VESICLES LOADED WITH BIOLOGICAL STRUCTURES, BIOPOLYMERS AND/OR OLIGOMERS

[76] Inventors: Yechezkel Barenholz, 18 Nevenh Shaannan St., Jerusalem, Israel, 93707; Lilianne K. Bar, Menuha Venahala 37/7, Rehovot, Israel; Dvorah Diminsky, Harazim 21, Jerusalem, Israel, 96181; Moshe Baru, Hadarim Street, Pardes-Hanna, Israel, 3700

[21] Appl. No.: 08/710,576

[22] Filed: Aug. 13, 1996

Related U.S. Application Data

[63] Continuation of application No. 08/592,437, filed as application No. PCT/EP94/02242, Jul. 8, 1994, abandoned.

[51] Int. Cl.[7] ............................ A61K 9/127; C12N 11/02; G01N 33/544; C07K 17/02
[52] U.S. Cl. .................. 424/450; 424/93.7; 424/94.1; 424/520; 435/177; 435/182; 436/528; 436/535; 514/2; 514/44; 530/812; 530/817
[58] Field of Search ...................... 435/174, 177, 435/180; 424/450, 93.7, 94.1, 520; 436/528, 535; 514/2, 44; 530/812, 817

[56] References Cited

U.S. PATENT DOCUMENTS 4,229,360  10/1980  Schneider et al. ...................... 260/403
4,235,871  11/1980  Papahadjopoulos et al. ............ 424/19

*Primary Examiner*—David M. Naff
*Attorney, Agent, or Firm*—Jacobson, Price, Holman & Stern, PLLC

[57] ABSTRACT

A composition useful for preparing vesicles loaded with biological cell-structures, biopolymers and/or -oligomers is prepared by solubilizing amphiphatic material such as a phospholipid in a polar-protic solvent miscible with water, solubilizing biological cell-structures, biopolymers and/or -oligomers in an aqueous medium, mixing the polar-protic solvent containing the amphiphatic material with the aqueous medium containing the biological cell-structures, biopolymers and/or -oligomers, and lyophilizing the resultant mixture to form a dry product. The dry product is hydrated in an aqueous medium to form the loaded vesicles. The polar-protic solvent may be tert-butanol, and the aqueous medium may contain a salt such as sodium chloride, an isoosmotic cryoprotectant such as lactose, sucrose or trehalose, or a mixture of the salt and the cryoprotectant. A medicament for disease treatment is formed by mixing the loaded vesicles with a pharmaceutically acceptable vehicle.

27 Claims, 3 Drawing Sheets

FACTOR IX CALIBRATION CURVE CLOTTING ASSAY $y = -0.10714 + 4.1086 \cdot 10^{-2} x \quad R^2 = 0.989$ $y = -0.19524 + 8.8943 \cdot 10^{-2} x \quad R^2 = 0.880$

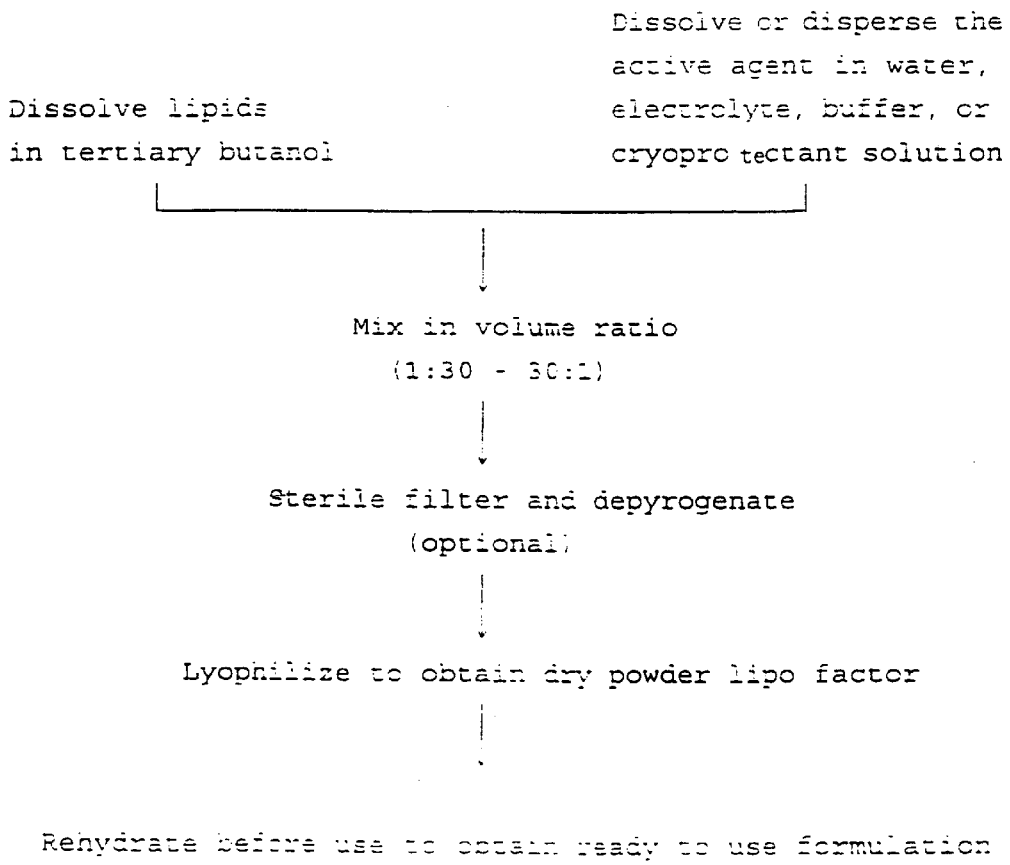

METHOD FOR PREPARATION OF VESICLES LOADED WITH BIOLOGICAL STRUCTURES, BIOPOLYMERS AND/OR OLIGOMERS

This is a continuation of application Ser. No. 08/592,437, filed Feb. 6, 1996, now abandoned, which is a national stage of PCT/EP94/02242 filed Jul. 8, 1994.

The invention is related to a method for preparation of vesicles loaded with biological structures, biopolymers and/or - oligomers, a formulation comprising vesicles loaded with biological structures, biopolymers and/or -oligomers obtainable according to the method of the invention, a medicament comprising the formulation of the invention as well as a method of treating diseases administering the medicament of the invention.

Several attempts have been tried to use lipid vesicles formed by natural or synthetic phospholipids as vehicles for the administration of effective substances.

Grey, A. and Morgan, J. report that liposomes were first described nearly a quarter of a century ago and have been useful models for studying the physical chemistry of lipid bilayers and the biology of the cell membrane. It was also realised that they might be used as vehicles for the delivery of drugs but clinical application have been slow to emerge. Proposed clinical uses have included vaccine adjuvancy, gene Transfer and diagnostic imaging but the major effort has been in the development of liposomes as targetable drug carriers in the treatment of malignancy. Although based on good in vitro data and animal studies, the strategies have been mostly impractical due to the predominant but unwanted uptake by the reticuloendothelial system and the limited extent of extravasation. The same features have nonetheless been turned to advantage in the case of amphotericin B which has recently become the first liposomally formulated agent to be licensed for parenteral use. Liposomal doxorubicin is currently also being evaluated in clinical trials. The early evidence suggests that while liposomal encapsulation may not greatly enhance their efficacy the toxicity of these agents is greatly attenuated (A. Gray, J. Morgan, "Liposomes in Haematology" in Blood Reviews, 1991, 5, 258–271).

Liposomes have been used in biological systems such as plasma extravascular space like reticuloendothelial system to more access celluar uptake of liposomes. Liposomes were loaded with amphotericin which is an effective but toxic antifungal. Antitumor agents like adriamycine have also be incorporated into liposomes. Vaccines and adjuvants as well as biological response modifiers like lymphocines and so on were studied in encapsulated form. Liposomes are discussed in field of a gene transfert as vehicles.

N. Sakuragawa et al. report in Thrombosis Research 38, 681–685, 1985, 1988 Clinical Hematology 29 (5) 655–661, that liposomes containing factor VIII have been prepared for oral administration to patients which are suffering from von Willebrand's disease. The encapsulation was carried out by dissolving the protein factor VIII concentrates in an aprotinin containing solution and transferred into lecithin coated flasks. After drying the flasks by rotation for 30 min under negative pressure liposomes were formed which entrapped factor VIII concentrates. The liposome solution was centrifuged yielding 40% of factor VIII entrapped in liposomes.

Another method for entrapment of drugs in liposomes is based on dehydration - rehydration. This is described by C. Kirby and G. Gregoriadis in Bio/Technology, November 1984, pages 979–984. In this preparation the entrapments can be increased by using additional lipid. Disclosed is the use of cholesterol as being of positive influence of the drug entrapment. Since cholesterol is involed in the pathobiochemistry of some disorders, administration of cholesterol containing vesicles is not harmless at all.

Object of the present invention is to provide a method for encapsulating biological structures, biopolymers and/or oligomers particularly those being pharmaceutically active into lipid membrane vesicles giving higher encapsulation of the respective substance. A further object is the preparation of a formulation particularly a medicament having a higher efficiency.

Surprisingly, one object of the invention is solved by a method for preparation of vesicles loaded with biological structures, biopolymers and/or -oligomers comprising the step of co-drying a fraction of amphiphatic material and a fraction of biological structures, biopolymers and/or -oligomers wherein said fraction of amphiphatic material is present in an organic solvent which is miscible with water and said fraction of biological structures, biopolymers and/or -oligomers is present in an aqueous medium.

Liposomes can be classified according to various parameters.

For example, when size and number of lamellae (structural parameters) are used than three major types of liposomes have been described: Multilamellar vesicles (MLV), small unilamellar vesciles (SUV) and large unilamellar vesicles (LUV). MLV are the species which form spontaneously on hydration of dried phospholipids above their gel to liquid crystalline phase transition temperature (Tm). Their size is heterogenous and their structure resembles an onion skin of alternating, concentric aqueous and lipid layers.

SUV are formed from MLV by sonication and are single layered. They are the smallest species with a high surface-to-volume ratio and hence have the lowest capture volume of aqueous space to weight of lipid.

A third type of liposome LUV has a large aqueous compartment and a single (unilamellar) or only a few (oligolamellar) lipid layers.

Further details are disclosed in D. Lichtenberg and Y. Barenholz, Liposomes: Preparation, Characterization, and Preservation, in Methods of Biochemical Analysis, Vol. 33, pp. 337–462, as exemplified in FIG. 3.

As used herein the term "loading" means any kind of interaction of the biopolymeric substances to be loaded, for example, an interaction such as encapsulation, adhesion (to the inner or outer wall of the vesicle) or embedding in the wall with or without extrusion of the biopolymeric substances.

As used herein, the term "liposome" is intended to include all spheres or vesicles of any amphiphatic compounds which may spontaneously or non-spontaneously vesiculate, for example phospholipids where at least one acyl group replaced by a complex phosphoric acid ester. The most of triacylglycerol is suitable and most common phospholipids for the present invention are the lecithines (also referred to as phosphatidylcholines (PC)), which are mixtures of the diglycerides of stearic, palmitic, and oleic acids linked to the choline ester of phosphoric acid. The lecithines are found in all animals and plants such as eggs, soybeans, and animal tissues (brain, heart, and the like) and can also be produced synthetically. The source of the phospholipid or its method of synthesis are not critical, any naturally occurring or synthetic phosphatide can be used.

Examples of specific phosphatides are L-α-(distearoyl) lecithin, L-α-(diapalmitoyl) lecithin, L-α-phosphatide acid, L-α-(dilauroyl)-phosphatidic acid, L-α(dimyristoyl) phosphatidic acid, L-α(dioleoyl)phosphatidic acid, DL-a (dipalmitoyl) phosphatidic acid, L-α(distearoyl) phosphatidic acid, and the various types of L-α-phosphatidylcholines prepared from brain, liver, egg yolk, heart, soybean and the like, or synthetically, and salts thereof. Other suitable modifications include the controlled peroxidation of the fatty acyl residue cross-linkers in the phosphatidylcholines (PC) and the zwitterionic amphiphates which form micelles by themselves or when mixed with the PCs such as alkyl analogues of PC.

The phospholipids can vary in purity and can also be hydrogenated either fully or partially. Hydrogenation reduces the level of unwanted peroxidation, and modifies and controls the gel to liquid/crystalline phase transition temperature ($T_m$) which effects packing and leakage.

The liposomes can be "tailored" to the requirements of any specific reservoir including various biological fluids, maintains their stability without aggregation or chromatographic separation, and remains well dispersed and suspended in the injected fluid. The fluidity in situ changes due to the composition, temperature, salinity, bivalent ions and presence of proteins. The liposome can be used with or without any other solvent or surfactant.

Another important consideration in the selection of phospholipid is the acyl chain composition thereof. Currently, it is preferred that it has an acyl chain composition which is characteristic, at least with respect to transition temperature ($T_m$) or the acyl chain components in egg or soybean PC, i. e., one chain saturated and one unsaturated or both being unsaturated. However, the possibility of using two saturated chains is not excluded.

The liposomes may contain other lipid components, as long as these do not induce instability and/or aggregation and/or chromatographic separation. This can be determined by routine experimentation.

A variety of methods for producing the modified liposomes which are unilamellar or multilamellar are known and available:

1. A thin film of the phospholipid is hydrated with an aqueous medium followed by mechanical shaking and/or ultrasonic irradition and/or extrusion through a suitable filter;
2. dissolution of the phospholipid in a suitable organic solvent, mixing with an aqueous medium followed by removal of the solvent;
3. use of gas-above its critical point (i. e., freons and other gases such as $CO_2$ or mixtures of $CO_2$ and other gaseous hydrocarbons) or
4. Preparing lipid detergent mixed micelles then lowering the concentration of the detergents to a level below its critical concentration at which liposomes are formed (Lichtenberg, Barenholz, 1988).

In general, they produce liposomes with heterogeneous sizes from about 0.02 to 10 μm or greater. Since liposomes which are relatively small and well defined in size are preferred for use in the present invention, a second processing step defined as "liposome down sizing" is for reducing the size and size heterogeneity of lioosome suspensions.

The liposome suspension may be sized to achieve a selective size distribution of vesicles in a size range less than about 5 μm and preferably to be ≦0.4 μm. Liposomes in this range can readily be sterilized by filtration through a suitable filter. Smaller vesicles also show less a tendency to aggregate on storage, thus reducing potentially serious blockage or plugging problems when the liposome is injected intravenously. Finally, liposomes which have been sized down to the submicron range show more uniform distribution.

Several techniques are available for reducing the sizes and size heterogeneity of liposomes, in a manner suitable for the present invention. Ultrasonic irradiation of a liposome suspension either by standard bath or probe sonication produces a progressive size reduction down to small unilamellar vesicles (SUVs) between 0.02 and 0.08 μm in size. Homogenization is another method which relies on shearing energy to fragment large liposomes into smaller ones. In a typical homogenization procedure the liposome suspension is recirculated through a standard emulsion homogenizer until selected liposome sizes, typically between about 0.1 and 0.5 μm are observed. In both methods, the particle size distribution can be monitored by conventional laser-beam particle size determination.

Extrusion of liposomes through a small-pore polycarbonate filter or equivalent membrane is also an effective method for reducing liposome sizes down to a relatively well-defined size distribution whose average is in the range between about 0.02 and 5 μm, depending on the pore size of the membrane. Typically, the suspension is cycled through one or two stacked membranes several times until the desired liposome size distribution is achieved. The liposome may be extruded through successively smaller pore membranes, to achieve a gradual reduction in lipsome size.

Centrifugation and molecular sieve chromatography are other methods which are available for producing a liposome suspension with particle sizes below a selected threshold less than 1 μm. These two respective methods involve preferential removal of large liposomes, rather than conversion of large particles to smaller ones. Liposome yields are correspondingly reduced.

The size-processed liposome suspension may be readily sterilized by passage through a sterilizing membrane having a particle discrimination size of about 0.4 μm, such as a conventional 0.45 μm depth membrane filter. The liposomes are stable in lyophilized form and can be reconstituted shortly before use by taking up in water.

BRIEF DESCRIPTION OF THE FIGURES

FIG. 3 shows a scheme for carrying out a method according to the invention.

Figure 1:
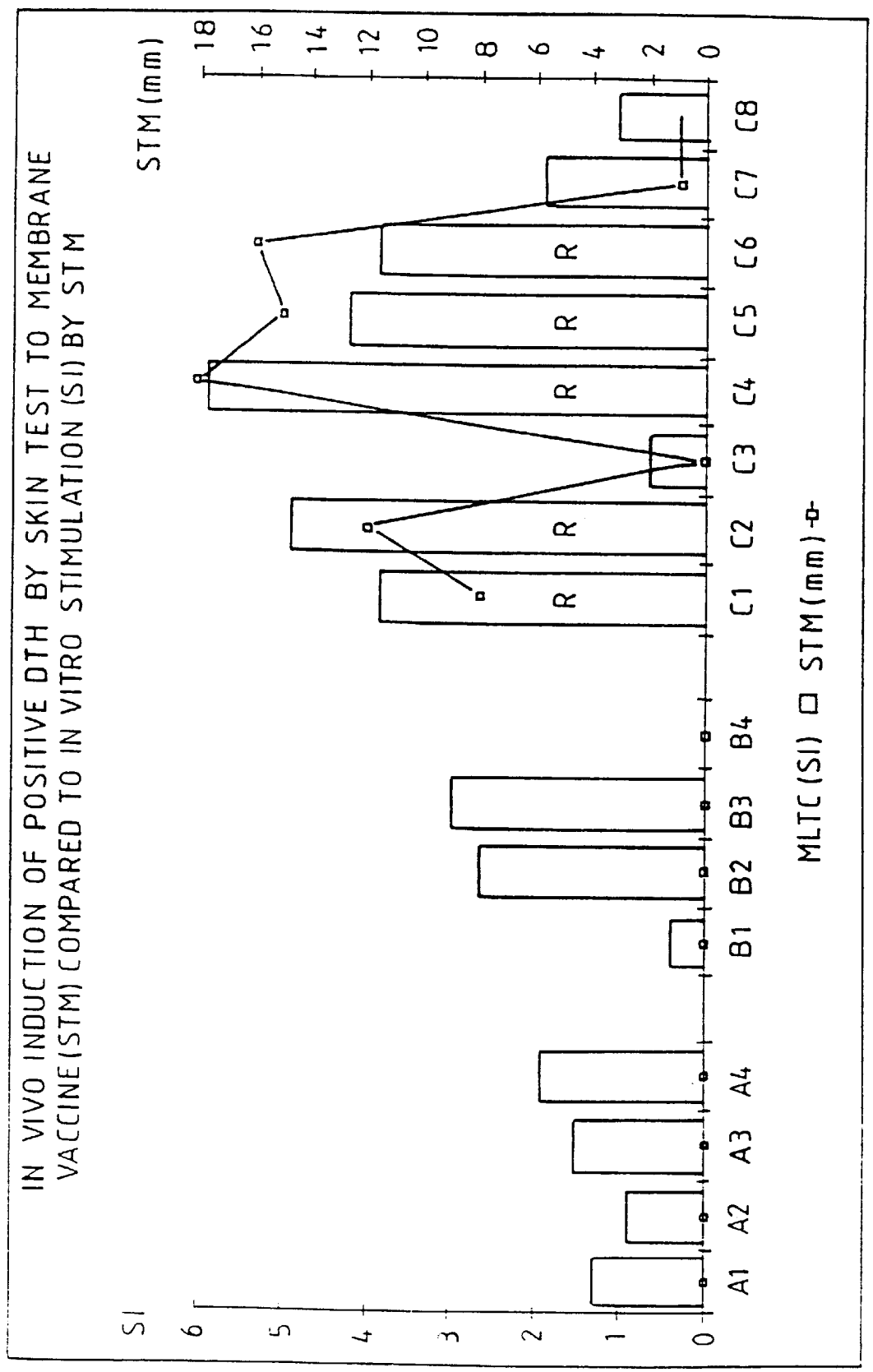
FIG. 1 is a graph showing the in vivo induction of positive delayed type hypersensitivity (DTH) by skin test membrane vaccine (STM), compared with in vitro stimulation (stimulation index—SI) by STM (mixed lymphocyte tumor culture—MLTC).

In a preferred embodiment the method of the invention comprises the steps:

a) solubilizing amphiphatic material in a polar-protic solvent being miscible with water (fraction A), alternatively, dried lipids or lipid mixture can be used in any form (powder, granular, etc.) directly, b) solubilizing biopolymers and/or oligomers in an aqueous medium being physiologically compatible, optionally having a salt content equivalent to up to 5% by weight, preferably 15% by weight of sodium chloride solution (fraction B)

c) mixing together the fractions A and B d) drying the fraction obtained in step c) with a method retaining the functional properties of said biological structures, biopolymers and/or oligomers.

In general, the lipids mentioned above are suitable to be used for forming lipid membrane vesicles. In particular saturated, unsaturated phospholipids and combinations thereof are advantageously used according to the method of the invention. Dimyristoyl phosphatidyl choline (DMPC) and/or dimyristoyl phosphatidyl glycerol (DMPG) are used more preferably for forming of the lipid vesicles. Preferably, the molar ratio of the DMPC: DMPG is between 1:20 and 20:1.

According to the method of the invention the organic solvent being miscible with water is a polar-protic solvent having solubilizing properties such as for example aliphatic alcohols with lower number carbon atoms so long as they mix with aqueous systems and do not affect adversely the effectivity of the biological structures, biopolymers and/or -oligomers to be encapsulated. Suitable alcohols are e. g. methanol, ethanol, propanol and/or preferably t-butanol.

Biological structures to be encapsulated according to the invention are any structures of higher order built up by various components and/or substructures. Examples for these structures are whole cells, such as natural or transformed B-cells, cell organelles, such as ribosoms or mitochondriae. Virions or particles such as hepatitis B surface antigen (HBsAg) particles. Biopolymers and/or -oligomers to be encapsulated according to the invention are any substances having effects in human or animal systems. Preferred are substances as proteins such as enzymes, proenzymes, cofactors, such as those of the blood clotting system, antigens, antibodies, factors the immune system such as complement factors, peptides such as hormones, nucleotides and/or nucleic acids such as genomic DNA for use in gene therapy, RNA such as MRNA, rRNA, tRNA, antisense RNA and the like.

It is understood the skilled person that the amount of organic polar-protic solvent miscible with water is strongly dependent on it interference with the substance to be encapsulated to the liposomes. For example, for HBsAg 50% is tolerable while factor IX (which is a clotting-factor) is to be encapsulated as an amount of approximately 30% of tert-butanol is tolerable. This may strongly vary with the nature of the substance to be encapsulated. For example, if factor IX which is a clotting factor is to be encapsulated an amount of about 30% of tertiary butanol is tolerable, whereas, factor VIII is much more sensitive to the impact of tert.-butanol. In this case an amount of less than 10% of tert.-butanol is preferred. The percentage of t-butanol in these examples is based on percent by volume calculated for final concentration.

According to the method of the invention it is preferred to keep the biopolymers and/or -oligomers in a medium having an ionic strength corresponding up to about 5% sodium chloride concentration with or without cryoprotectant which is a pharmaceutically acceptable agent such as lactose, sucrose or trehalose, preferably the medium for solubilizing, dissolving or dispersing the biological structures, biopolymers and/or -oligomers is an aqueous solution of about 0.9% by weight sodium chloride and/or an isoosmotic cryoprotectant.

According to the invention any method for drying is suitable so long as the effectivity of the biological structures, biopolymers and /or -oligomers are not affected adversely by the selected drying method. The function of the biological structures, biopolymers and/or oligomers to be loaded are mostly retained when mild drying conditions are selected. For example removing of the solvents of the solution of the biological structures, biopolymers and/or -oligomers and the lipids is favorably achieved by drying under reduced pressure at slightly elevated temperatures at maximum. The resistance of the active substances to be loaded depend strongly on the stability the respective biopolymer and/or -oligomer. For example, nucleic acids are more stable versus impact of heat on their structure and function than proteins. The latter are more sensitive to heat-denaturation. A very preferred method for co-drying of the fractions according to the invention is the method of lyophilisation (freeze drying). This method is a mild drying procedure for almost all of the active biological structures, biopolymers and/or oligomers which become liposomal loaded according to the invention.

According to the method of the invention the product obtained as described above in dry form is taken up in an aqueous medium. Thereby, liposomes formed become loaded with the respective biological structures, biopolymers and/or oligomers. The system typically forms a dispersion.

According to the method of the invention a novel formulation is provided comprising lipid membrane vesicles loaded with biological structures, biopolymers and/or -oligomers. The formulation of the invention preferably is in a solid state, which is available after the co-drying of fraction A and B, eventually having other pharmaceutically acceptable vehicles and/or adjuvants as well as other pharmaceutically active agents.

Another preferred embodiment of the formulation of the invention comprises a solution of the fraction in an aqueous medium obtainable according to the method of the invention. Preferably, the aqueous medium for taking up the dry fraction of the formulation contains a balanced salt content in order to adjust the conditions of the formulation in such a manner that the aqueous solution thus obtained can readily be used as a medicament. Typically, the formulation tends to form a dispersion after being taken up into water.

Thus, the medicament of the invention is basically the formulation obtainable by the method of the invention but being adapted to a way of administration which is suitable for the treatment or prophylaxis of the respective disease.

For example, the medicament of the invention can be administered by topical, oral, intravenous, pulmonary, intraperitioneal, intranasal, rectal, intraocular, buccal, subcutaneous and intramuscular ways of application.

A method of treatment and/or prophylaxis of diseases by administering an effective amount of the medicament according to the invention is provided. It is understood by the skilled person that the dosage is depending on the concentration of the effective substances as well as their efficiency. According to the method of treatment and/or prophylaxis of the invention preferably a dosage of up to 2,000 mg vesicles (e. g. phospholipid liposomes)/kg body weight is administered to the patient. The accurate dosage can vary dramatically. The variation, however, depends on e. g. the type and efficacy of the substance encapsulated in the liposomes, the efficiency of the encapsulation reaction itself (being high with the method of the invention), the kind of administration and the like. The respective parameters can be easily optimized by the person skilled in the art and can be regarded as being routine experiments.

The invention is further explained by the following non-limiting examples.

EXAMPLE 1

Preparation of Samples of Anti-HBV Liposomal Vaccine

The following samples of vaccine, designated samples 1, 2, 3 and 4 were prepared using the method of the invention.
Sample 1

A mixture of DMPC : DMPG in a molar ratio of 9:1 respectively was prepared in tert.-butanol. An aqueous HBsAg solution such as 0.9% NaCl in 1:1 (v/v) was added. The final HBsAg: phospholipids (w/w) ratio was 0.0015. The solution was frozen and dried by lyophilisation. A dry powder was obtained which was reconstituted before use with double distilled sterile pyrogen-free water. Multilamellar liposomes were formed; loading efficiency of HBsAg was 97%. "Empty liposomes" were prepared similarly by mixing 1 vol of aqueous solution of 0.9%. NaCl with 1 vol of lipid solution in tertiary butanol.

The extent of HBsAg exposure on the liposome surface of sample 1 and liposome size was determined. It was found that the size of these lipsomes was 4.5 μm and the exposure of the antigen on the liposome surface was tested. It was found that the titer of antibodies which was developed was high and sufficient to protect against infection by HBV (see Table 1). The titer was similar to that obtained in mice that were vaccinated with the same antigen using aluminum hydroxide based vaccine except for the high dose of injected antigen (2.5 μg) in which the liposomal vaccine was inferior: injection of this dose to mice in the control group stimulated the highest titer of antibodies.

Sample 2

Liposomes loaded with HBsAg and "empty liposomes" were prepared as described for sample 1. A group of seven Balb/c mice, six weeks old, were vaccinated by 0.09 g HBsAg loaded in liposomes which were diluted with "empty liposomes" and 0.9% NaCl. The final injection volume was 0.5 ml/mice, which included also 1 mg/kg mice of the immunomodulator MTP-PE in POPC/DOPS (7:3 mole ratio) liposomes. After 35 days the level of anti-HBs in the mice was measured. The titer of antibodies was twice the titer which developed after injecting the same dose of antigen without MTP-PE (sample 1).

Sample 3

Liposomes loaded with HBsAg and identical "empty liposomes" were prepared as described for sample 1 with one difference in that the aqueous solution used for lipid hydration also contained 5% lactose. The liposomes were frozen and dried. A powder was obtained which was reconstituted before use with sterile pyrogen-free bidistilled water. The liposomes were characterized for their size, percentage of antigen loading and the extent of antigen exposure on the liposome surface. The immunization efficacy of the preparation was tested in Balb/c mice, six weeks old. The mice were divided into three groups, five mice in each group, and the animals were vaccinated using three doses of antigen: 0.09 μg, 0.27 μg, 0.81 μg, respectively. Anti-HBs was measured after 35 days (see Table 1). A high titer of antibodies was observed which should be sufficient to protect against HBV infection.

Injecting this preparation in low doses of antigen (0.09 μg) to mice resulted in development of the highest titer of antibodies, compared with the titer which was obtained with all other preparations including the mice group which was vaccinated with the commonly used aluminum hydroxide-based vaccine having identical HBsAg.

Sample 4

Liopsomes loaded with HBsAg were prepared as described for sample 3. Three groups of five Balb/c mice, six weeks old, were vaccinated with four doses of HBsAg at a level of 0.09 μg, 0.27 μg, 0.81 μg, respectively. The total injection volume was 0.5 ml/mice. The liposomes were diluted with PBS only and not with "empty liposomes" and therefore the amount of lipid varied and increased with increasing protein level. After 35 days the mice were bled and their serum antibody titer was determined. The results show a high titer of antibodies which should be sufficient to protect against infection by HBV.

TABLE 1

Summary of anti-HBs titer (mIU/ml) using the liposomal vaccine samples described in Example 1

| Sample No. | μm HBsAg injected | | | |
|---|---|---|---|---|
| | 0.09 | 0.27 | 0.81 | 2.5 |
| 1 | 52.4 ± 18.6 | 426.7 ± 206.3 | 4,953.2 ± 1,211.5 | 6,692.0 ± 854.5 |
| 2 | 106.1 ± 16.5 | — | — | — |
| 3 | 193.3 ± 69.1 | 1,664.6 ± 392.8 | 2,701.4 ± 203.6 | — |
| 4 | 55.0 ± 17.3 | 895.9 ± 384.6 | 1,527.7 ± 166.6 | — |
| Control Alum-based vaccine | 40.0 ± 13.6 | 396.6 ± 73.1 | 6,749.3 ± 2,342.5 | 17,465.3 ± 2,967.0 |

EXAMPLE 2

Stability of Liposomal HBsAc Vaccine After Storage at Various Temperatures

As described above hepatitis vaccines known in the art used aluminum hydroxide as adjuvant and stabilizer. The disadvantage of the aluminum hydroxide-based vaccines is that they cannot be frozen nor can they be stored beyond 8° C. These vaccines thus have to be stored between 2–8° C. to maintain their efficacy.

There are three parameters to demonstrate stability of a vaccine under different conditions:
1. Efficiency (measure immunogenicity).
2. Chemical stability (measssure hydrolysis of lipids; measure protein to lipid ratio).
3. Physical stability (measure size of particle).

The stability of the vaccine was tested after storage at three temperature (a) −20° C., (b) 2–6° C. and (c) room temperature.

The results obtained were as follows:
(a) The vaccine stored at −20° C. was effective after 1 month or more and was chemically and physically stable after 1.5 years and more.
(b) The vaccine stored at 2–6° C. was effective after 1 month and more and was chemically and physically stable after 1.5 years and more.
(c) The vaccine stored at room Temperature was chemically and physically stable after 1.5 years or more.

These results demonstrate that the vaccine of the invention in form of liposomes is stable over a wide temperature range.

Since the current hepatitis vaccines lose their immunogenicity during freezing it is unexpected that the liposomvaccine of the invention retains its activity both during the freezing step of the freeze drying process and also during storage of the vaccine below 0° C.

Thus, the advantage of HBV vaccine of the invention is evident. It does not need to be stored in a refrigerator and is not sensitive to freezing. The distribution of such a vaccine is greatly simplified especially in third world countries where the need for a vaccine against hepatitis B is greatest; additionally a vaccine which may be frozen aids distribution in countries such as Russia and China were the ambient temperature is often below freezing.

Applicants have thus produced a novel liposomal based HBsAg vaccine which is stable both below zero degrees and at room temperature, i. e. The vaccine may be stored under suboptimal conditions.

EXAMPLE 3

Preparation and Characterization of Factor-IX-Loaded Liposomes

Two different methods of liposome preparation will be compared for stability and Factor IX encapsulation.

(a) Dehydrated Reydrated Vesicles (DRV's)
(b) Lipid and drug co-solubilization in an organic solvent.
(a) Dehydrated Rehydrated Vesicles (DRV's)

Preparation of multilamellar vesicles loaded with Factor-IX by the DRV method require the following steps: preparation of small unilamellar vesicles (SUV's) in bidistilled water, mixing them with a solution of factor IX previously dialyzed against amino acids and flash-frozen the mixture. After lyophilization, multilamellar vesicles loaded with Factor-IX were obtained by rehydrating the preparation with bidistilled water, then stepwise saline is added, until the final liposomes concentration was reached. At this point the multi-lamellar vesicles can be sized by extrusion to obtain oligo-lamellar or small unilamellar vesicles.

Rehydration of lyophilized material with minimal volume results in an increase of the overall concentration of the factor. After liposomes are formed the solution can be further diluted without affecting the loading efficiency, and this is reflected in the concentration of the material that is actually loaded. Since liposomes are osmotically active, losses of material on exposure to hypotonic media during all manipulations subsequent to hydrating were minimzed by dialyzing the Factor before mixing with the SUV's to obtain a lower osmolarity in the liposome interior during the rehydration step.

(b) Lipid and Drug Co-Solubilization in an Organic Solvent

In this preparation lipid solubilized in tert-butanol is mixed with an aqueous solution of the factor to obtain an homogeneous solution. The solution is frozen and the solvent removed by lyophilization. Mulitlamellar vesicles loaded with Factor-IX are obtained by hydration of the dry mixture, firstly in small volume of bidistilled water, then stepwise with saline, until the final liposome concentration is reached. At this point the multlamellar vesicles can be sized by extrusion to obtain oligolamellar or small unilamellar vesicles.

Determination of Factor IX Activity

Factor IX activity was measured by a clotting assay. In this assay the percent of factor IX activity can be determined by the degree of correction obtained when a dilution of the tested sample is added to the factor IX Deficient Plasma (purchased from Baxter Diagnostics Inc.). The measuring instrument is called ACL-Automated Coagulation Laboratory from Instrumentation Labortory (Italy).

Figure 2:
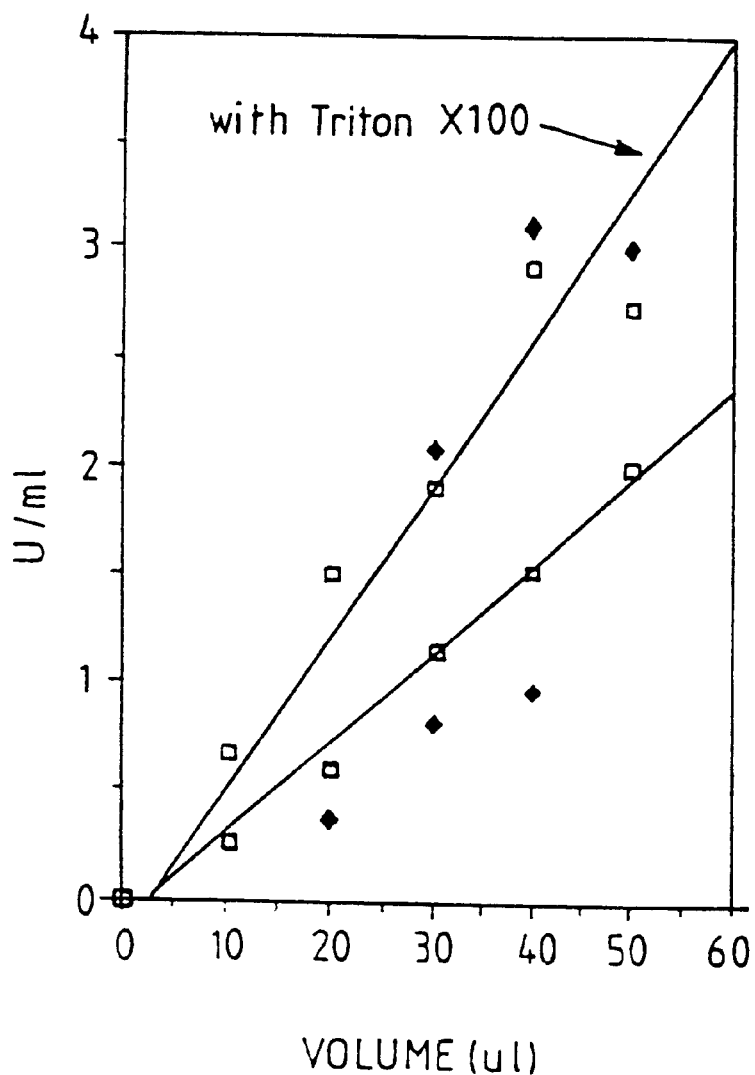
FIG. 2 shows a calibration curve constructed for the clotting assay of factor IX.

A calibration curve was first constructed for the clotting assay of factor IX, using appropriate dilutions of a stock solution of ca. 50 U/ml. FIG. 2 shows a good fit to a linear regression ($R^2$=0.989).

Liposomes containing factor IX were pelleted by centrifugation in an Eppendorff centrifuge at 12,000 g for 10 min and the factor IX activitiy was determined in the supernatants and pellet. The pellet was solubilized prior analysis with Triton X-100. A concentration dependency on factor IX activity with Triton X100 was found. 1% Triton X100 (final concentration) caused a 50% loss of activity, while no loss was observed at 0.2%. In general, the total activity of the factor was recuperated, namely, the activity of the super-natants and pellet was always similar or even higher than the inital activity of the preparation. The loading efficiency was higher than 80%.

EXAMPLE 4

Melanoma Treatment of Human Patients by Liposomal Vaccine Containing Allogenic Human Melanoma Vaccine Prepared Using Tertiary Butanol Vaccine preparation A mixture of DMPC:DMPG in a molar ratio of 9:1 respectively was dissolved in tert-butanol in a 1:6.7 w/v ratio. The mixture was heated and stirred until the lipids were dissolved. After sterile filtration, sterile water was added to the organic mixture until a 1: 1 (v/v) ratio between the tert-butanol and the water was reached. An aqueous solution of the melanomic membrane mixture was added to a 1:750 protein : phospholipids (w/w) ratio. This final mixture was divided in single doses of 1 g phospholipids and each one was frozen and dried by lyophilization. A dry powder was obtained and stored at −70° C. Prior to application liposomes were formed by rehydration in double distilled, sterile and pyrogen-free aqueous solution containing 0.9% NaCl to obtain a liposome dispersion of 10% phospholipid concentration. After reconstitution, this liposomes had an average size of 1 $\mu$m and an average phospholipid: protein ratio of 765:1.

Treatment

A three arm randomized study for the treatment of melanoma by asi alone and either systemic or regional interleukin-2.

Clinical and immunological

Evaluation: eligible:

PTS with metastatic diseases;

ECOP PS 1–2: no previous

Immunother.; positive to 3/7 antigens (marieux).

Cimetidine 800 mg × 2/daily 4 weeks

Vaccine in liposomes

200 $\mu$g protein/sile, (se), at 2 sites, 10 weekly immunizations

RANDOMIZATION

A Melanoma vaccine only-given on day 1. cimetidine 800 mg×2/daily.

B Melanoma vaccine only given on day 1, followed by IV IL-2, at one million units/msq. on consecutive days 2, 3, 4. cimetidine 800 mg×2/daily.

C Melanoma vaccine given on day 1, followed by subcutaneous IL-2 at vaccine site, concomitantly, IL-2 dose: 50.000 units/site at two sites, on days 1,2 & 3. Cimetidine 800 mg×2/daily.

| PAT | PROT | TREATMENT | DISEASE | RESPONSE | OUTCOME |
|---|---|---|---|---|---|
| #1 | A | CIM + 4X V CC | Lung | PD (2 m) Lung/Br/Liver | Dead (4 m) |
| #2 | A | CIM + 2X VACC | SC | PD (2 m)Brain | Dead (6 m) |
| #3 | A | CIM + 5X VACC | LN/LIVER | PD (2 m) LN/Liver | Alive (6 m) |
| #4 | A | CIM + 5X VACC | LN/Liver | PD (2 m) LN/Liver | Alive (6 m) |
| #1 | B | CIM + 10X VACC + IL2 S | Liver | PD (3.5 m)/Liver/Bone | Dead (8 m) |
| #2 | B | CIM + 10X VACC + IL2 S | LN/Bone | PD (4 m) LN/Bone | Alive (16 m) |
| #3 | B | CIM + 10X VACC − IL2S | LN | PD (4 m) LN/Lung | Alive (13 m) |
| #4 | B | CIM + 6X VACC + IL2 S | LN | PD? (sepsis) | Dead (2.5 m) |
| #1 | C | CIM + 10X VACC + IL2 R | LN/Lung | CR (8 m) LN/Lung | Alive (13 m) NED |
| #2 | C | CIM + 10X VACC + IL2 R | LN | CR (9 m) LN | Alive (13 m) NED |
| #3 | C | CIM + 10X VACC + IL2 R | LN/Liver | PD (3 m) LN/Liver | Dead (6 m) |
| #4 | C | CIM + 10X VACC + IL2 R | LN/Lung | PR (4 m) LN(PR)/Lung (CR) | Alive (12 m) Surg NED |
| #5 | C | CIM + 10X VACC + IL2 R | SC/Liver/Bone | PR (5 m) SC(PR)/Liver (CR) | Dead (9 m) PD Brain |
| #6 | C | CIM + 10X VACC + IL2 R | SC/Lung | MixR (5 m) SC (PD)/Lung (CR) | Alive (11 m) IPL NED |
| #7 | C | CIM + 7X VACC + IL2 R | SC/LN/Liver | PD (3 m) SC/Liver | Dead (5 m) |
| #8 | C | CIM + 5X VACC + IL2 R | SC/Lung/Liver | PD (1.5 m) SC/Liver/Lung | Alive (2 m) |

CR=complete response
PR=partial response
SC=stable condition
m=month (1) Allogeneic human melanoma vaccine was prepared from membranes of six melanoma cell lines which express both class I and II MHC antigens and MAAs (by R24 and P97) MoAbs);

(2) Membranes were loaded in liposomes consisting of DMPC: DMPG in a 9:1 molar ratio, were tested for sterility, pyrogenicity and tumorigenicity in nude mice;.

(3) 16 PTS, (patients) were treated by vaccine (FIG. 1): 4—vaccine only (A); 4—vaccine+systemic IL2 (B); and 8—by vaccine+low-dose, regional (C) IL2;

(4) Clinical responses (regression of metastases) were observed in 5 of 8 PTS in arm C of the protocol;

(5) The above clinical responses correlated with de novo induction-of cutaneous DTHI to membrane vaccine preparation (STM) and in vitro MLTC (proliferative) responses to STM;

(6) Augmented cytolytic responses against melanoma cell lines were observed in the majority of vaccine-treated PTS, but these were not MHC-restricted, nor did they show any correlation with clinical responses;

(7) Selective anti-melanoma cytolytic responses following IVS (in vitro stimulation) were observed when 18 h—instead of 4 h assay was used, suggesting CD4, T-cell response, also corroborated by surface markers study;

(8) In parallel patients were vaccinated with the same antigens given as alumm based vaccine without any response.

EXAMPLE 5

Candidemia Treatment in Mice by Liposomal Vaccine Containing Candida Ribosomes

Vaccine Preparation

DMPC: DMPG at a 9:1 molar ratio were dissolved in tert-butanol in a 1:10 (w:v) ratio and the lipid mixture was pre-warmed to dissolve the lipids completely. An aqueous ribosomal mixture containing 1.5 mg ribosomes/ml (determined by Orcinol) was added to the lipids at a 1:100 w/w final ratio. In some cases Lipid-A was added at this stage as an adjuvant in a 1:1,000 lipid-A to phospholipids molar ratio. This suspension was frozen and lyophilized in aliquouts of 0.5 g phospholipids and the dry powder was stored at −20° C. Prior application liposomes were formed by adding two aliquots of 0.5 ml volume of double distilled, sterile and pyrogen free aqueous solution containing 0.9% NaCl.

Treatment

Four groups of five Balb/c mice, six weeks old, were vaccinated with a one single dose of 100 µg ribosomes. Two weeks later a booster injection was given and twenty eight days after the first immunization the mice were challenged by intravenous infection with $10^4$ Candida albicans cells.

Group a: buffer (TMB) and IFA (incomplete Freund adjuvant).
Group 2: ribosomal mixture and IFA
Group 3: liposomes containing ribosomes
Group 4: liposomes containing ribosomes and lipid-A.

This experiment was repeated twice and the results are summarized in the following table.

TABLE 3

|  | Group 1 | Group 2 | Group 3 | Group 4 |
|---|---|---|---|---|
| Mortality | 6/9 | 2/10 | 0/10 | 0/10 |
| Percentage | 67% | 20% | 0% | 0% |

EXAMPLE 6

Preparation of Liposomes Containing Antihaemophilic Factor IX

Liposomes Preparation

Purified egg yolk phosphatidylcholine was dissolved in tert-butanol at various ratios and the mixture was slightly warmed until the phospholipid was dissolved. Double distilled sterile, pyrogen free water was added until the desired ratio between the organic solvent and the water was reached. An aqueous solution of salt free Factor IX (OCTANYNE®) adjusted pH 7.4 was added to the suspension under continuous mixing and subsequently lyophilized. The ratio of the total protein to phospholipid was 1:400 (w/w). The dry mixture was stored at 40° C. Liposomes of 1 µm average size were prepared by hydrating the powder with aliquots of sterile, pyrogen-free double distilled water and mixing well between the additions. The last addition consisted of saline to raise the salt concentration to isosmotic conditions.

We claim:

1. A method for preparation of a composition useful in preparing vesicles loaded with biological cell-structures, biopolymers or -oligomers by co-drying a fraction of amphiphatic material and a fraction of biological cell-structures, biopolymers or -oligomers wherein said fraction of amphiphatic material is present in an organic solvent which is miscible with water and said fraction of biological cell-structures, biopolymers or -oligomers is present in an aqueous medium, comprising the steps of a) solubilizing amphiphatic material in a polar-protic solvent miscible with water to effect fraction A, b) solubilizing biological cell-structures, biopolymers or -oligomers or mixture of biopolymers and oligomers in a physiologically compatible aqueous medium, optionally having a salt content equivalent to up to a 5% by weight sodium chloride solution, to effect fraction B, c) mixing together the fractions A and B, and d) lyophilizing the fraction obtained in step c).

2. A method for preparing a composition useful in preparing loaded vesicles, from an organic-solvent fraction and an aqueous fraction, comprising the steps of:

a) solubilizing an amphiphatic material in a polar-protic solvent miscible with water to effect fraction A, b) solubilizing biological cell-structures, biopolymers or -oligomers, or combination of biopolymers and -oligomers in a physiologically compatible aqueous medium, to effect fraction B, c) mixing together the fractions A and B to obtain a mixed fraction, which contains the polar-protic solvent and the aqueous medium, and d) lyophilizing the mixed fraction to give a dry product.

3. The method of claim 2 wherein the amphiphatic substance is selected from the group consisting of saturated and unsaturated phospholipids, and mixtures thereof, and mixtures with cholesterol of saturated and unsaturated phospholipids, and mixtures thereof.

4. The method of claim 3, wherein the phospholipids are hydrogenated or non-hydrogenated soybean derived phospholipids, egg yolk phospholipids, dimyristoyl phosphatidyl choline, dimyristoyl phosphatidyl glycerol, or mixture thereof.

5. The method of claim 4, wherein the phospholipids comprise a mixture of dimyristoyl phosphatidyl choline and dimyristoyl phosphatidyl glycerol at a molar ratio of dimyristoyl phosphatidyl choline:dimyristoyl phosphatidyl glycerol between 1:20 and 20:1.

6. The method of claim 2, wherein said polar-protic solvent is tert-butanol.

7. The method of claim 2, wherein the biological cell-structures are natural or transformed B-cells, ribosomes, or mitochondriae; the biopolymers or -oligomers are enzymes, proenzymes, cofactors, virions, or virion surface antigens, antigens, antibodies, complement factors, hormones, nucleotides, DNA, mRNA, rRNA, tRNA, or antisense RNA.

8. The method of claim 2, wherein the physiologically compatible aqueous medium is a solution of about 0.9% by weight sodium chloride, isoosmotic cryoprotectant, or mixture thereof.

9. The method of claim 8, wherein the cryoprotectant is lactose, sucrose, or trehalose.

10. The method of claim 2 further comprising the step of hydrating the dry product in an aqueous medium to form liposomes.

11. The method of claim 2, wherein the physiologically compatible aqueous medium has a salt content equivalent to up to a 5% by weight sodium chloride solution.

12. The dry product made by the method of claim 2.

13. The dry product made by the method of claim 3.

14. The dry product made by the method of claim 4.

15. The dry product made by the method of claim 5.

16. The dry product made by the method of claim 6.

17. The dry product made by the method of claim 7.

18. The dry product made by the method of claim 8.

19. The dry product made by the method of claim 9.

20. The liposomes made by the method of claim 10.

21. A medicament comprising the dry product of claim 12 reconstituted with water in combination with a pharmaceutically acceptable vehicle.

22. A medicament comprising the dry product of claim 13 reconstituted with water in combination with a pharmaceutically acceptable vehicle.

23. A medicament comprising the liposomes of claim 20 in combination with a pharmaceutically acceptable vehicle.

24. A method of treating disease by administering to a patient an effective amount of the medicament according to claim 21.

25. A method of treating disease by administering to a patient an effective amount of the medicament according to claim 22.

26. A method of treating disease by administering to a patient an effective amount of the medicament according to claims 23.

27. Method of claim 25 wherein the effective amount is a dosage of up to 2,000 mg, measured by phospholipid per kg body wt.

* * * * *